United States Patent [19]

Butland

[11] Patent Number: 5,599,578

[45] Date of Patent: Feb. 4, 1997

[54] TECHNIQUE FOR LABELING AN OBJECT FOR ITS IDENTIFICATION AND/OR VERIFICATION

[76] Inventor: Charles L. Butland, 6204 Vista del Mar, #474, Playa del Rey, Calif. 90293

[21] Appl. No.: 333,077

[22] Filed: Nov. 1, 1994

Related U.S. Application Data

[63] Continuation-in-part of Ser. No. 8,620, Jan. 22, 1993, Pat. No. 5,360,628, which is a continuation-in-part of Ser. No. 597,859, Oct. 15, 1990, Pat. No. 5,194,289, which is a continuation-in-part of Ser. No. 263,058, Oct. 27, 1988, abandoned, which is a continuation-in-part of Ser. No. 868,955, May 30, 1986, Pat. No. 4,882,195, which is a continuation-in-part of Ser. No. 857,929, Apr. 30, 1986, abandoned.

[51] Int. Cl.$^6$ ............................................. B41M 3/14
[52] U.S. Cl. .................. 427/7; 427/157; 427/160; 427/250; 427/288; 427/384
[58] Field of Search .................. 427/7, 288, 157, 427/265, 384, 261, 256, 160

[56] References Cited

U.S. PATENT DOCUMENTS

| | | | |
|---|---|---|---|
| 3,886,083 | 5/1975 | Laxer | 427/7 |
| 4,387,112 | 6/1983 | Blach | 427/7 |
| 4,546,595 | 9/1985 | Acitelli et al. | 427/7 |
| 5,139,812 | 8/1992 | Lebacq | 427/1 |

FOREIGN PATENT DOCUMENTS

| | | | |
|---|---|---|---|
| 2118928 | 11/1971 | Germany | 427/7 |

*Primary Examiner*—Janyce Bell
*Attorney, Agent, or Firm*—Mueller and Smith, LPA

[57] ABSTRACT

The present invention is addressed to providing a simple, yet reliable method for labeling an object for its verification. The present invention includes applying a mark to said object with a visible ink which contains a first component which is visible to the naked eye and a second component which is invisible to the naked eye and comprises one or more of ultraviolet radiation (UV) dye which is visible only in the presence of selected ultraviolet radiation, an infrared (IR) dye which is visible only in the presence of selected infrared radiation, an ink which displays a selected measurable electrical resistivity, or a biologic marker. The applied mark has said first component which is visible to the naked eye and said second component which is invisible to the naked eye.

16 Claims, No Drawings

TECHNIQUE FOR LABELING AN OBJECT FOR ITS IDENTIFICATION AND/OR VERIFICATION

CROSS-REFERENCE TO RELATED APPLICATIONS

This application is a continuation-in-part of U.S. application Ser. No. 08/008,620, filed Jan. 22, 1993, now U.S. Pat. No. 5,360,628, which in turn is a continuation-in-part of U.S. application Ser. No. 07/597,859, filed Oct. 15, 1990, now U.S. Pat. No. 5,194,289, which in turn is a continuation-in-part of U.S. application Ser. No. 07/263,058, filed Oct. 27, 1988, now abandoned, which in turn is a continuation-in-part of U.S. application Ser. No. 868,955, filed May 30, 1986, now U.S. Pat. No. 4,882,195, which in turn is a continuation-in-part of U.S. application Ser. No. 857,929, filed Apr. 30, 1986, now abandoned, the disclosures of which are expressly incorporated herein by reference.

BACKGROUND OF THE INVENTION

The present invention relates to the labeling of objects for verifying authenticity and more particularly to the use of a selectively-perceptible mark in combination with a visibly-perceptible mark for labeling of objects.

Many objects require verification for authenticity. Such objects include paintings, sculptures, cartoon cells, sports and other collectibles, and like works of art; video cassette recorders, televisions, and like household objects; and computers; printers, and like office and business equipment. Other instances of identification in order to verify ownership, include, for example, records, audio and video tape cassettes, computer software recorded on floppy disks or diskettes, perfumes, designer clothes, handbags, briefcases, cartoon cells, automobile/airplane parts, securities (e.g., stock certificates), wills, and like objects. Many American industries have been plagued by a flagrant piracy explosion over the past decade involving many of the foregoing products. Often, these objects have no serial number or other unique means of identification, or the number can be removed easily following a theft. Alternatively, counterfeiting of such objects has become a thriving business and the need to identify authentic from counterfeit objects is of great importance. Thus, a simple method for reliably identifying or authenticating such objects would be welcomed by the owners, the manufacturers of such objects, and even the U.S. Customs Service.

BROAD STATEMENT OF THE INVENTION

The present invention is addressed to providing a simple, yet reliable method for labeling an object for its verification. The present invention includes applying a mark to said object with a visible ink which contains a first component which is visible to the naked eye and a second component which is invisible to the naked eye and comprises one or more of ultraviolet radiation (UV) dye which is visible only in the presence of selected ultraviolet radiation, an infrared (IR) dye which is visible only in the presence of selected infrared radiation, an ink which displays a selected measurable electrical resistivity, or a biologic marker. The applied mark has said first component which is visible to the naked eye and said second component which is invisible to the naked eye.

Advantages of the present invention include a simple, yet reliable means for labeling objects for identification. Another advantage is that a portion of the label is not perceptible to people absent the application of special techniques in order to determine the presence of such labels. Another advantage is that the label can last for an almost indefinite period of time. A yet further advantage is the ease and versatility for identification which is afforded by the present invention. These and other advantages will become readily apparent to those skilled in the art based upon the disclosure contained herein.

DETAILED DESCRIPTION OF THE INVENTION

Once an object is identified and verified, it can be labeled in accordance with the inventive technique disclosed herein so that its authentication at a later date is materially enhanced. For present purposes, "permanent" as applied to the present labeling technique on the object means that the label is incapable of being removed from the object in the ordinary course of intended handling and usage of the object for a time adequate for identification and/or verification of the object to occur. For some objects, it may be desirable that the label remain affixed to the object and identifiable for many years. Such objects would include works of art, household and business appliances, machinery, automobiles, automobile parts, records, video audio tape cassettes, computer software diskettes, and the like. It is conceivable that some objects would require verification for only a limited time (e.g., for several days to several months); however, it is believed that extended verification time periods will find greater acceptance in the market place.

The present invention includes the recognition that in order to stop counterfeiting of, for example, consumer goods, a visible mark must be present on the object. A first mark or indicia which is readily perceptible to the naked or (mechanically) unaided eye, then, is applied to the object. Such a visible mark would include a picture, signature, visible fingerprint, or other convention identification mark generated by a visible ink. Thus, a level of protection in ascertaining the authenticity of the object is provided by the visible mark.

The second means of identification and/or verification is invisible to the owner (and the copyist). The functions of the combination of visible and invisible marks includes the designed difficulty with which the copyist should be faced in duplicating both marks and the ability to field test the authenticity in many instances by use of invisible light radiation (UV or IR), an electrical probe measuring electrical resistivity, and the like. Such "invisible" marks include, for example, ultraviolet (UV) dyes, infrared radiation dyes, electrical resistivity inks, and biologic markers. UV dyes and their application in identification can be found in U.S. Pat. No. 5,194,289 cited above. IR 140 is 5,5'-dichloro-11-diphenylamino-3,3'-diethyl-10, 12-ethylenethiatricarbocyanine perchlorate (CAS 53655-17-7) and it will absorb energy and reemit it at a longer wavelength (i.e., far infrared range of the spectrum). Since the reemitance wavelengths can be viewed at a selected nanometer wavelength, use of an infrared converter and "night vision" goggles for intensifying the image, then, enables the viewing of such reflected wavelengths of energy which cannot be perceived by the naked or unaided eye.

A preferred phosphor is a rare earth oxysulfide, such as selected froth those phosphors as described in British patent application 2,258,659 published on Feb. 17, 1993, this disclosure of which is expressly incorporated herein by reference. Such phosphors are described as doped yttrium oxysulphide ($Y_2O_2S$), in which the dopants comprise, by weight of the oxysulphide, 4% to 50% of one or both of erbium (Er) and ytterbium (Yb). The material may comprise 1 to 50 ppm of one or more other lanthanide elements. Erbium and ytterbium may be replaced by thulium (Tm), holmium (Ho), or lutetium (Lu). The material may be in the form of particles whose average size is no more than 20 µm. Reference also is made to O'Yocom, et al., "Rare-Earth-Doped Oxysulfides for Gallium Arsenide-Pumped Lumines Devices", *Met. Trans.*, (1971), 2(3), 763–767, and Wittke, et at., "Erbium-Ytterbium Double Doped Yttrium Oxide. New Red-Emitting Infrared-Excited Phosphor", *J. Appl. Phys.*, (1972), 43(2), 595–600, the disclosures of which are expressly incorporated herein by reference.

Electrically conductive inks which utilize electrically-conductive particles is yet another technique for "invisibly" labeling an object. The visible mark itself could be applied to the object using inks that exhibit a predetermined electrical resistivity. Use of electrically-conductive pigments, e.g., carbon, silver, gold, copper, aluminum, or the like, renders the ink electrically conductive which enables its resistivity to easily measured even in the field. In fact, use of magnetic particles, (e.g., iron oxide) may even produce ink that can be identified by its magnetic properties.

Another technique utilizes biologic markers, such as amino acids and proteins as disclosed in U.S. Pat. No. 5,194,289, cited above. Such biologic materials can be profiled by gas chromatography which creates a standard for later comparison with a small (e.g., nanogram) sample of ink from a "stolen" object labeled in accordance with the precepts of the present invention. Additionally, U.S. Pat. No. 5,139,812 discloses the use of nucleic acid sequences in ink for identifying an object with a probe. U.S. Pat. No. 4,880,750 discloses the use of individual-specific antibodies (e.g., in an ink) for identification of security documents. U.S. Pat. No. 4,441,943 uses synthetic polypeptides for labeling explosives. The disclosures of these citations are expressly incorporate herein by reference. Such techniques also are not readily perceptible without the aid of special equipment and/or chemicals which develop the presence of such markers. For present purposes, such markers are unique and not easily (if at all) replicated by the forger or counterfeiter. The foregoing biologic markers may be incorporated into a visible or an invisible ink for use in labeling objects. It should be understood also that such biologic markers can be native or can be synthetic, including fragments, single chains, and a variety of additional forms currently developed or yet to be developed. It may even be feasible to radiolabel some biologic or other markers and determine their presence thereby.

The present invention can be implemented readily and has versatility in that a variety of techniques can be used to identify and/or verify an object. Several of the identification techniques can be implemented in the field, while others require laboratory equipment and processing. Combining such techniques permits screening in the field with later absolute verification coming from laboratory analysis. Such ease of use and versatility adds to the effectiveness of the present invention as a deterrent to crime and as an identification/verification of goods technique.

With respect to a preferred phosphor as described above (e.g., gallium oxysulfide), such up-converting phosphors require high (peak power) density photon radiation in order to excite emission. A 10 Hz pulsed LED in the 880 nm region of the spectrum with approximately 50 mW peak power should be suitable therefor. With respect to the detector equipment, a simple illuminator can be used where human perception of a greenish glow to determine the presence of the security phosphor is employed.

Another proposed illuminator/detector could be manufactured from a flashing LED with a very narrow pulse width due to the fact that human perception is unnecessary. Such detector could have an optical filter that blocks IR illumination frequency and passes only the frequency of radiation emitted by the phosphor, i.e., target frequency. Such a detector could be used under high ambient light conditions. Such a detector could be configured as a simple swipe-type reader or could have a hinged or removable gate to expose the phosphor to the LED.

A proposed illuminator/detector/reader could have the ability to read encoded patterns of the embedded phosphor, such as, for example, a bar code. The reading capability can be provided by suitable software, such as bar code reader engines.

It will be observed that the present invention has apparent utility in a wide variety of fields beyond those described herein. The disclosure herein illustrates the presently-known preferred embodiments for utilizing the labeling technique of the present invention. It will be readily apparent to those skilled in the art that a wide variety of other objects may be suitably labeled in accordance with the precepts of the present invention for their identification and/or verification. Such additional objects and circumstances are included within the scope of the present invention in accordance with the precepts thereof. All citations referred to herein are incorporated expressly herein by reference.

I claim:

1. Method for labeling an object for identification which comprises the step of:
    applying a mark to said object with a visible ink which contains:
    (a) a first component which is visible to the naked eye; and
    (b) a second component which is invisible to the naked eye and which is one or more of ultraviolet radiation (UV) dye which is visible only in the presence of ultraviolet radiation, an infrared (IR) dye which is visible only in the presence of infrared radiation, an ink which displays a measurable electrical resistivity, or a biologic marker selected from one or more of a protein, amino acid, DNA, polypeptide, hormone, or antibody,
    said mark having said first component which is visible to the naked eye and said second component which is invisible to the naked eye.

2. The method of claim 1, wherein said visible ink housed in a pen.

3. The method of claim 1, wherein said visible ink contains a UV dye and a biologic marker.

4. The method of claim 1, wherein said visible ink contains an IR dye and a biologic marker.

5. The method of claim 4, wherein said IR dye comprises a phosphor.

6. The method of claim 5, wherein said phosphor comprises a rare earth oxysulphide.

7. The method of claim 6, wherein said phosphor is a gallium oxysulfide.

8. The method of claim 1, wherein said visible ink contains two or more of said second components.

9. The method of claim 1, wherein said IR dye comprises a phosphor.

10. The method of claim 9, wherein said phosphor comprises a rare earth oxysulphide.

11. The method of claim 10, wherein said phosphor is a gallium oxysulfide.

12. Method for labeling an object for identification which comprises the step of:

applying a mark to said object with a visible ink which contains:
(a) a first component which is visible to the naked eye; and
(b) a second component which is invisible to the naked eye and which is one or more of ultraviolet radiation (UV) dye which is visible only in the presence of ultraviolet radiation, an infrared (IR) dye which is visible only in the presence of infrared radiation, or a biologic marker selected from one or more of a protein, amino acid, DNA, polypeptide, hormone, or antibody, said mark having said first component which is visible to the naked eye and said second component which is invisible to the naked eye.

13. The method of claim 12, wherein said visible ink contains an IR dye and a biologic marker.

14. The method of claim 13, wherein said IR dye comprises a phosphor.

15. The method of claim 14, wherein said phosphor comprises a rare earth oxysulphide.

16. The method of claim 15, wherein said phosphor is a gallium oxysulfide.

\* \* \* \* \*